(12) United States Patent
Latta et al.

(10) Patent No.: US 6,614,519 B1
(45) Date of Patent: Sep. 2, 2003

(54) SURFACE INSPECTION TOOL USING A PARABOLIC MIRROR

(75) Inventors: Milton Russell Latta, San Jose, CA (US); Wai Cheung Leung, San Jose, CA (US); Bob C. Robinson, Hollister, CA (US); Timothy Carl Strand, San Jose, CA (US); Andrew Ching Tam, Saratoga, CA (US)

(73) Assignee: International Business Machines Corporation, Armonk, NY (US)

( * ) Notice: Subject to any disclaimer, the term of this patent is extended or adjusted under 35 U.S.C. 154(b) by 347 days.

(21) Appl. No.: 09/696,864

(22) Filed: Oct. 25, 2000

(51) Int. Cl.$^7$ ................................................ G01N 21/88
(52) U.S. Cl. ................................ 356/237.2; 356/237.1
(58) Field of Search ................ 356/237.1, 237.2–237.5, 356/239.7, 239.8, 600, 445, 446, 429–431; 250/559.01, 559.04–559.07, 559.09; 359/202, 203, 212

(56) References Cited

U.S. PATENT DOCUMENTS

| | | | |
|---|---|---|---|
| 3,790,287 A | | 2/1974 | Cuthbert et al. |
| 4,441,124 A | * | 4/1984 | Heebner et al. ............ 348/126 |
| 4,464,050 A | | 8/1984 | Kato et al. |
| 4,954,723 A | | 9/1990 | Takahashi et al. |
| 5,381,225 A | | 1/1995 | Kohno |
| 5,448,364 A | | 9/1995 | Moran |
| 5,528,360 A | | 6/1996 | Kohno |
| 5,541,413 A | * | 7/1996 | Pearson et al. ......... 250/339.11 |
| 5,581,353 A | | 12/1996 | Taylor |
| 5,875,029 A | * | 2/1999 | Jann et al. .................. 356/450 |
| 5,898,492 A | | 4/1999 | Imaino et al. |
| 5,917,589 A | | 6/1999 | Imaino et al. |
| 5,923,419 A | | 7/1999 | Thomas |

* cited by examiner

*Primary Examiner*—Richard A. Rosenberger
*Assistant Examiner*—Vincent P. Barth
(74) *Attorney, Agent, or Firm*—G. Marlin Knight

(57) ABSTRACT

An inspection system using laser light directed at an off-axis parabolic mirror which focuses the beam on the surface being inspected and also serves as the collector for scattered and specular light returned from the surface is described. Specular and scattered light returned from the surface onto the parabolic mirror is divided into appropriate fields and directed onto detectors. In the preferred embodiment a polarized laser is used in conjunction with a polarizing beam splitter and a quarter-wave plate to route the reflected beam to a detector while allowing the original beam to be directed through the same optics. The parabolic mirror and selected additional components may be commonly mounted on a translatable stage which is moved along a radius of the disk when the optical inspection is being performed. Other components of the system such as the laser can remain in a fixed position. The system of the invention can be used to inspect one or both planar surfaces of the disk by providing duplication of selected components appropriately oriented with respect to the second surface.

15 Claims, 3 Drawing Sheets

SURFACE INSPECTION TOOL USING A PARABOLIC MIRROR

FIELD OF THE INVENTION

The invention relates to the field of automated optical surface inspection and more particularly to optical systems for inspection of planar surfaces.

BACKGROUND OF THE INVENTION

The density of information stored on magnetic disks used in disk drives requires that the surfaces of the disk be formed with extreme precision and that the inspection processes identify defects of microscopic size. In addition to optical inspection other tests typically include glide tests and selective magnetic tests. The quantity of magnetic information which can be stored on a disk is too large to allow cost effective testing of all of the magnetic bit locations and, therefore, only a small subset of surface is typically magnetically tested. Optical inspection requires less time than magnetic testing and is more cost effective for large scale manufacturing. It is also sometimes desirable for a test stand to be used which is capable of performing different kinds of tests by utilizing multiple heads which perform the individual tests. Compact test head design in such a multitest system is an important consideration. The ability to test or inspect both planar surfaces of the disk is also desirable.

Prior art systems include the commonly assigned U.S. Pat. No. 5,898,492 which uses reflected light from the disk surface and captures scattered light from piano mirrors positioned at an angle above the surface. The described system uses a telecentric lens assembly and a rotating polygon scanner to direct both the incident light and combined reflected and scattered light. The system is suitable for simultaneous inspection of both surfaces of a disk. In this system the disk is not rotating while being inspected rather is moved linearly through the scanning area while the inspection apparatus remains in a fixed position. This design is poorly suited to the multihead tester application where the space constraints are more stringent.

SUMMARY OF THE INVENTION

The surface being inspected in a preferred embodiment is a highly reflective thin film magnetic disk for use in a disk drive. The invention uses laser light directed at an off-axis parabolic mirror which focuses the beam on the disk surface and also serves as the collector for scattered and specular light returned from the surface. The selection of the parabolic mirror allows the system to be made extremely compact for use in a multitester application and allows inspection of both sides of a disk simultaneously by positioning a parabolic mirror above and below the disk. The parabolic mirror is oriented with its axis parallel to a radial line on the disk surface. Specular and scattered light returned from the surface onto the parabolic mirror is divided into appropriate fields and directed onto detectors. Two or more piano mirrors can conveniently be used to separate the light into fields by placing the mirrors in series by using concentric apertures in the mirrors. In the preferred embodiment a polarized laser is used in conjunction with a polarizing beam splitter and a quarter-wave plate to route the reflected beam to a detector while allowing the original beam to be directed through the same optics.

When used in a multi-station test tool, preferably the parabolic mirror and selected additional components are commonly mounted on a translatable stage which is moved along a radius of the disk when the optical inspection is being performed. Other components of the system, the laser, for example, can remain in a fixed position.

In an embodiment of the invention the disk is mounted on a spindle that provides rotatable support and which is connected to a motor for rotating the spindle and the disk. The system of the invention can be used to inspect one or both planar surfaces of the disk by providing duplication of selected components appropriately oriented with respect to the second surface. The system includes at least a first parabolic mirror that is radially positionable over the planar surface to capture specular light and at least a portion of scattered light from the portion of the planar surface to be inspected. The laser beam is conditioned and directed by optical components onto the parabolic mirror and then focused onto the planar surface. In the preferred orientation, the parabolic mirror captures a portion of scattered light and specular light coming from the surface. The light captured by the parabolic mirror is then separated into at least two fields: one containing the specular light and one or more fields of scattered light. These fields of light are directed to appropriate detectors.

DETAILED DESCRIPTION OF THE INVENTION AND THE PREFERRED EMBODIMENTS

Although the parabolic mirror system of the invention can be used in a stand-alone tester, its use in a multi-station tester will be described. From the description below the embodiment of the invention in the simpler stand-alone environment will be straightforward. Likewise, the invention will be described primarily in conjunction with its use to inspect magnetic disk surfaces, but similar planar surfaces such, for example, as an optical disk surface or a semiconductor wafer surface could also be inspected using the invention.

Figure 1:
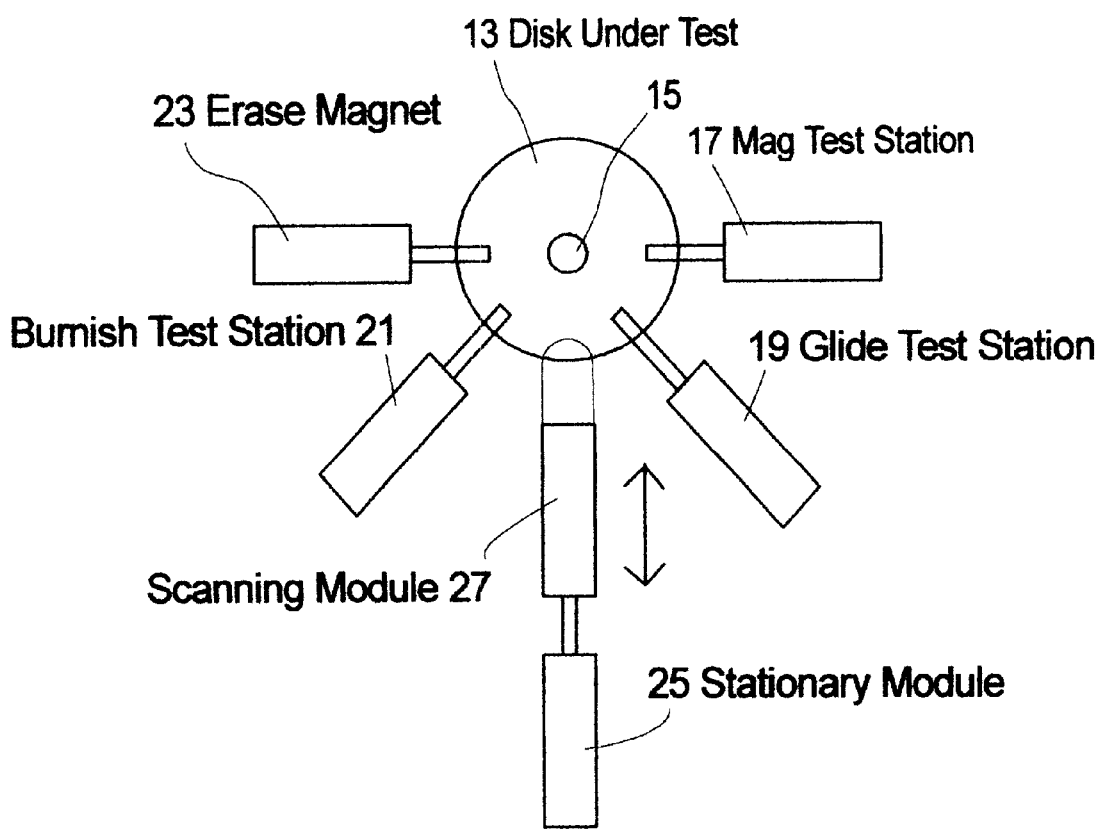
FIG. 1 is a block diagram of a multi-station tester in which the invention can be embodied.

FIG. 1 is a plan view block diagram of a multi-station tester 11 for magnetic disks in which the invention can be embodied. The disk under test 13 is mounted on spindle 15 that is rotated by a motor which is not shown. The disk can be loaded into the multi-station tester 11 by any means including manual loading or a robot arm (not shown). Examples of possible conventional test stations include a magnetic test station 17, a glide test station 19 and a burnish test station 21. An erase magnet 23 may also be included. The optical station according to the preferred embodiment of the invention is divided into a stationary module 25 and a scanning module 27 that is movable or translatable along a path which is parallel to a radius of the disk under test 13. The scanning module 27 can conveniently be precisely positioned by conventional means such as a voice coil motor or a lead screw driven by a stepper motor (not shown). The scanning module is preferably movable in a straight line along a radius of the disk. When the scanning module is stationary at a particular point along its path it scans a ring-shaped area as the disk rotates under it. The scanning module can be continuously moved along the radius to scan a spiral area.

The size of the incident spot made by the laser beam on the surface is an important factor in determining the resolution of the inspection system. A smaller spot size aids in increasing the resolution. For the inspection of magnetic disks specified for 15 gigabits per square inch, a spot size of 10 microns is adequate. Indexing the scanning module to a second point on the radius results in another ring-shaped area being scanned. It is preferable for the scanned rings to overlap. The scanning module has a linear movement large enough to allow scanning of the entire area of the disk required to be inspected. Since a disk for use in a disk drive has a hole in the center, the scanning module would need to move between a first position at which the focal spot on the disk is located at or near the outer edge and a second position at which the focal spot is located at or near the edge of the central hole.

Figure 2:
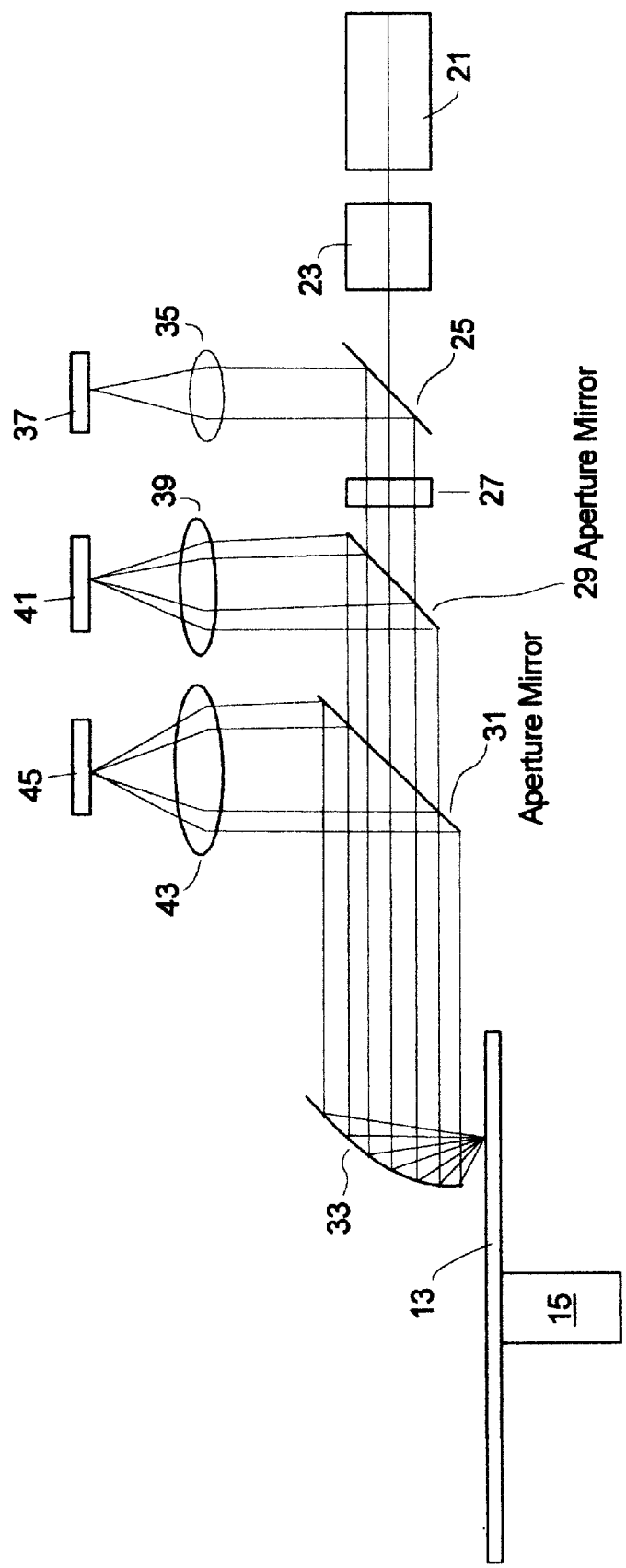
FIG. 2 is a schematic diagram of the optics in an embodiment of the invention for inspecting one side of a disk.

FIG. 2 is a schematic diagram of the optics and ray traces in an embodiment of the invention for inspecting one side of a disk. A two channel embodiment will have a second set of optics including a second parabolic mirror for the scanning module for the second surface which will be further discussed below. The laser 21 is preferably a linearly polarized laser having either a vertical or horizontal polarization. A collimated CW 532 nanometer laser is preferred by the applicants for use in the described embodiment In a two channel embodiment the laser beam may be split to serve both channels or each channel may have a dedicated laser. Conventional beam shaping optics 23 are used to initially collimate and focus the beam. After the initial shaping the beam is directed through polarizing beam splitter 25 which passes essentially all of the linearly polarized beam. A quarter-wave plate 27 is then used to change the polarization to circular, e.g., right-hand-circular (RHC). The beam then passes through the apertures in aperture mirrors 29, 31. The beam then strikes parabolic mirror 33 which is oriented with its axis parallel to the planar surface of disk 13. This arrangement results in the beam being directed onto the planar surface of the disk with a substantially orthogonal incidence. For a submicron detection capability the applicants' selected spot size is 10 microns.

If the spot where the beam strikes the disk is very flat, the beam will be reflected with minimal scattering back along the path of the incident beam, i.e., as specular light. The specular light will be reflected by the parabolic mirror back through the two aperture mirrors onto the quarter-wave plate 27. If the initial circular polarization is RHC polarization, it will have been changed to left-hand-circular (LHC) at this point after an odd number of reflections, i.e., two from the parabolic mirror and one from the disk surface. The quarter-wave plate 27 changes the LHC polarization to linear polarization orthogonal to the input polarization; thus, for example, if the input polarization is vertical, then the polarization of the specular beam will be horizontal at this point. The linearly polarized beam is reflected by the polarizing beam splitter to the detector lens 35 that focuses the specular light on the specular detector 37. The specular detector 37 is preferably position sensitive in order to capture the additional information about the surface features that is conveyed in the position of the specular light on the specular detector in addition to the intensity of the specular light.

The fact that the beam is circularly polarized and has a perpendicular incidence when it strikes the disk surface is an advantage of the invention. Unlike system's using linearly polarized light and non-normal incidence, the applicants system is not sensitive to defect orientation.

Irregularities in the surface will result in some of the light being scattered. In general, the deeper the surface feature, the more the incident beam will be scattered. Additionally there is an inverse relationship between the lateral size of small features and the angular extent of scattered light from these features. The parabolic mirror serves to collimate the scattered light. The angular cone covered by the parabolic mirror determines how much of the high angle scattered light is captured. It is preferable to collect as much of the high angle scattered light as practical, since this determines the minimum detectable feature size. In practice the limits on the size of the parabolic mirror that can be used will be determined by mechanical factors of the application such as the clearance between the disk surface and other components in the system, the mass that can be precisely positioned, etc. An effective inspection system embodying the invention need not have a 90 degree collection cone angle. Applicants have demonstrated effective inspection using the system of the invention with a 50 degree collection cone angle.

In alterative embodiments, a single scattered light field could be detected or more than two scattered light fields could be detected. This design choice can be made by balancing the system complexity and cost versus the information needed to effectively identify defects or features on the surface.

In the described embodiment the scattered light is separated into two fields representing small angle scattered light and large angle scattered light, the apertures in mirrors 29 and 31 are made concentric with the aperture in mirror 31 being larger than the aperture in mirror 29. The sizes of the apertures are not critical to operation of the system, but in general the aperture in mirror 29 should be sized to fully transmit the $1/e^2$ diameter of the input beam and allow some tolerance for alignment. The aperture in mirror 31 should preferably be sized to transmit approximately one half of the maximum angular collection of the parabolic mirror to the small angle detector. This arrangement will approximately divide the scattered light collected by the parabolic mirror equally between the two scattered light detectors. If a third scattered light detector is added, the apertures should preferably be sized to divide the scattered light into thirds and so forth. Aperture mirror 29 is arranged to reflect onto a focusing lens 39 and a detector 41 for small angle scattered light. Aperture mirror 31 is arranged to reflect onto a focusing lens 43 and a detector 45 for large angle scattered light.

Figure 3:
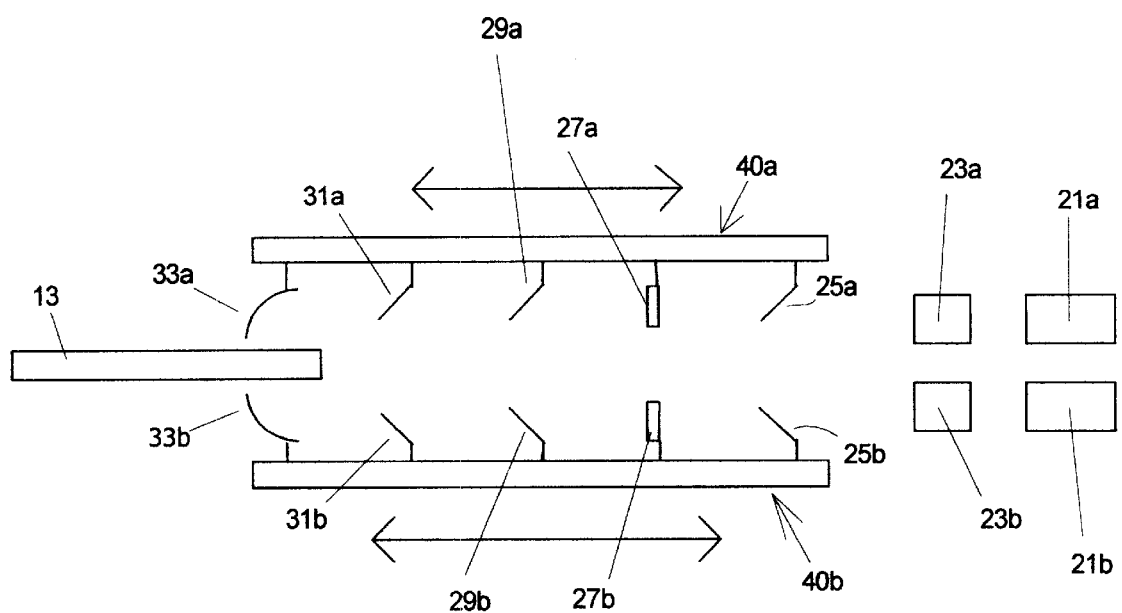
FIG. 3 is a schematic side view diagram of the optics in an embodiment of the invention for inspecting two planar surfaces of an object.

FIG. 3 is schematic side view of a two channel embodiment of the invention for inspecting the two planar surfaces of a surface simultaneously. The elements shown in FIG. 3 are labeled with an "a" suffix for the first channel which is for the upper surface and a "b" suffix for the second channel which is for the bottom surface. The scanning module for each channel has a stage 40a, 40b for mounting the components which are moved with the parabolic mirrors 33a, 33b. Although the stages are not shown as being mechanically connected for simplicity, it is preferable for the stages to be interconnected, in effect forming a single stage that is driven by a single positioning mechanism (not shown). The commonly mounted components are the aperture mirrors 31a, 31b, 29a, 29b; the quarter-wave plates 27a, 27b and the nonpolarizing beam splitters 25a, 25b. The fixed components include the beam shaping optics 23a, 23b and the lasers 21a, 21b. The translatable stage for the parabolic mirrors can be designed to move linearly along a radius of a disk which is being rotated. If a non-disk surface is being inspected, an X-Y translatable stage could be used to position the parabolic mirrors at selected spots to sufficiently cover the surfaces without the need to rotate the object.

The processing of the signals from the detectors is outside of the scope of the invention being claimed herein, but can be performed using known techniques such as those described in U.S. Pat. No. 5,898,492 titled "Surface Inspection Tool Using Reflected and Scattered Light" and U.S. Pat. No. 5,917,589 titled "Surface Inspection Tool." The scattered light channels are "zero background," since a perfectly flat surface will result in a zero signal from these channels. The specular light channel can be made zero background by operating the position sensitive detector in differential mode. The zero background mode improves signal-to-noise ratio and enhances the utilization of the dynamic range of the electronics.

One advantage to using the optical inspection of the invention in a multitester device is that the results of the various tests can be correlated to a much higher degree of precision than is possible when separate testers are used. Not all optical detects result in a magnetic defect. When the tests can be run on the same tester, it allows for specific magnetic testing of an area containing an optical defect to determine whether it corresponds to a magnetic defect. This correlates testing results in manufacturing efficiencies of saved time and fewer false rejections.

The foregoing description of an embodiment of the invention is not intended to suggest that the invention is limited to use to this embodiment. To the contrary, alterative embodiments will be readily apparent to practitioners of the art which will be within the spirit and substance of the invention.

What is claimed is:

1. A surface inspection tool comprising:
   a support for an object having at least a first planar surface;
   a source of a laser beam;
   a first parabolic mirror positionable at selected spots over the first planar surface with an axis oriented to focus the laser beam on the first planar surface and to capture specular light and at least a portion of scattered light from the first planar surface;
   a first aperture mirror mounted between the source of the laser beam to allow the laser beam and the specular light to pass through the aperture and for directing a portion of scattered light captured by the first parabolic mirror onto a first detector; and
   optics for directing specular light captured by the parabolic mirror onto a second detector.

2. The surface inspection tool of claim 1 wherein the first parabolic mirror is mounted with an axis oriented parallel to a radial line on the first planar surface and the laser beam is traveling parallel to the radial line on the fist planar surface when it strikes the parabolic mirror.

3. The surface inspection tool of claim 2 wherein the object is a disk further comprising a movable support on which the first parabolic mirror is mounted and means for positioning the parabolic mirror over a plurality of positions along a radius of the disk by changing the position of the movable support.

4. The surface inspection tool of claim 3 wherein the optics for directing specular light and the first aperture mirror are commonly mounted on the movable support.

5. The surface inspection tool of claim 5 further comprising a second aperture mirrors positioned coaxially with the first aperture mirror, the second aperture mirror having a smaller aperture the first aperture mirror and being positioned farther away from the parabolic mirror than the first aperture mirror to direct a portion of the scattered light passing through the first aperture mirror to a third detector while allowing specular light reflected from the planar surface to pass through the apertures of first and second aperture mirrors.

6. The surface inspection tool of claim 1 wherein the laser beam initially has a first linear polarization and the optics for directing the laser beam include a polarizing beam splitter and a quarter-wave plate which changes the first linear polarization to a circular polarization and the optics for directing specular light include an odd number of reflections and the quarter-wave plate which changes the circular polarization of the specular light to a second linear polarization orthogonal to the first linear orientation and the polarizing beam splitter which reflects the specular light having the second linear polarization to the second detector.

7. The surface inspection tool of claim 2 wherein the second detector is a position sensitive specular detector.

8. A method for inspecting a surface of a disk comprising the steps of:
   rotating the disk;
   positioning a parabolic mirror over a planar surface of the disk;
   directing a laser beam onto the parabolic mirror;
   focusing the laser beam on the planar surface;
   capturing specular light reflected from the planar surface and at least a portion of scattered light from the planar surface in the parabolic mirror;
   directing a portion of the scattered light captured by the parabolic mirror onto a first detector using a first aperture mirror positioned to allow the specular light to pass through the aperture; and
   directing the specular light captured by the parabolic mirror onto a second detector.

9. The method of claim 8 wherein the first parabolic mirror is mounted with an axis oriented parallel to a radial line on the first planar surface and step of directing the laser beam further comprises directing the laser beam along a path parallel to the radial line on the first planar surface of the disk to strike the parabolic mirror.

10. The method of claim 8 further comprising the step of moving the parabolic mirror over a plurality of positions along a radius of the disk by changing the position of a movable support for the parabolic mirror.

11. The method of claim 9 wherein the step of moving the parabolic mirror concurrently moves the first and second detectors.

12. The method of claim 8 wherein the laser beam initially
   has a first linear polarization and the method further comprises the steps of:
   directing the laser beam through a quarter-wave plate to change the first linear polarization to a first circular polarization;
   directing the specular light which has a second circular polarization due to being reflected and odd number of times through a quarter-wave plate to change a second circular polarization to a second linear polarization orthogonal to the first linear polarization; and
   reflecting the specular light with the second linear polarization onto the second detector.

13. An optical inspection system comprising:
   a rotatable support for a disk;
   a translatable stage;
   first and second parabolic mirrors attached to the translatable stage, the first and second parabolic mirrors being mounted in a confronting manner separated by a gap which allows the first and second parabolic mirrors to be positioned over first and second sides of a disk mounted on the rotatable support to collimate light which is scattered from first and second spots on first and second sides of a disk;

means for generating first and second laser beams;

optical means for directing the first laser beam onto the first parabolic mirror to focus the first laser beam on the first side of a disk;

optical means for directing the second laser beam onto the second parabolic mirror to focus the second laser beam on the second side of a disk; and at least first and second detectors onto to which a portion of the scattered light from first and second spots is directed after being collimated by first and second parabolic mirrors; and first and second aperture mirrors positioned to reflect a portion of the scattered light from first and second spots respectively to first and second detectors.

14. The optical inspection system of claim 13 further comprising first and second specular light detectors which receive light which passes through apertures in the first and second aperture mirrors respectively.

15. The optical inspection system of claim 14 wherein the first and second specular light detector are position sensitive specular light detectors.

* * * * *